(12) United States Patent
Zemenchik et al.

(10) Patent No.: US 10,820,475 B2
(45) Date of Patent: Nov. 3, 2020

(54) AGRICULTURAL IMPLEMENT AND PROCEDURE FOR ON-THE-GO SOIL NITRATE TESTING

(71) Applicant: CNH Industrial America LLC, New Holland, PA (US)

(72) Inventors: Robert A. Zemenchik, Kenosha, WI (US); Matthew Huenemann, Racine, WI (US)

(73) Assignee: CNH Industrial America LLC, New Holland, PA (US)

( * ) Notice: Subject to any disclaimer, the term of this patent is extended or adjusted under 35 U.S.C. 154(b) by 541 days.

(21) Appl. No.: 15/499,434

(22) Filed: Apr. 27, 2017

(65) Prior Publication Data
US 2018/0310464 A1    Nov. 1, 2018

(51) Int. Cl.
| | |
|---|---|
| *G01V 3/38* | (2006.01) |
| *A01B 79/00* | (2006.01) |
| *A01B 63/16* | (2006.01) |
| *A01B 76/00* | (2006.01) |
| *G01N 33/24* | (2006.01) |
| *G01N 21/3563* | (2014.01) |

(Continued)

(52) U.S. Cl.
CPC ............ *A01B 79/005* (2013.01); *A01B 63/16* (2013.01); *A01B 76/00* (2013.01); *A01C 21/007* (2013.01); *G01N 21/3563* (2013.01); *G01N 33/24* (2013.01); *A01B 63/111* (2013.01); *A01C 5/062* (2013.01); *G01N 2033/245* (2013.01)

(58) Field of Classification Search
CPC ....... A01B 79/005; A01B 63/16; A01B 76/00; A01C 21/007; G01N 21/3563; G01N 33/24

USPC .......................................................... 702/5
See application file for complete search history.

(56) References Cited

U.S. PATENT DOCUMENTS

| | | | |
|---|---|---|---|
| 5,461,229 A | 10/1995 | Sauter et al. | |
| 6,138,590 A | * 10/2000 | Colburn, Jr. | ......... A01B 79/005 |
| | | | 111/118 |

(Continued)

FOREIGN PATENT DOCUMENTS

WO    2015/171908 A1    11/2015

OTHER PUBLICATIONS

Extended European Search Report dated Sep. 17, 2018 for European Patent Application No. 18 16 6595 (8 pages).

(Continued)

*Primary Examiner* — Michael P Nghiem
(74) *Attorney, Agent, or Firm* — Rebecca L. Henkel; Rickard K. DeMille

(57) ABSTRACT

An agricultural implement includes a chassis and a shank or shanks carried by the chassis. The shank or shanks include an on-the-go nitrate-N sensor or sensors. Nitrate-N conditions are determined for at least first and second zones at different soil depths, either by multiple sensors carried on one or multiple shanks during a single pass of the agricultural implement, a single sensor carried first at the first depth and thereafter at the second depth during multiple passes of the agricultural implement, or a sensor moved between the first and second zones during a single pass of the agricultural implement. Rates for applying additional nitrogen can be calculated from the determined conditions, and the application rates and determined conditions can be mapped.

3 Claims, 3 Drawing Sheets

(51) Int. Cl.
*A01C 21/00* (2006.01)
*A01B 63/111* (2006.01)
*A01C 5/06* (2006.01)

(56) References Cited

U.S. PATENT DOCUMENTS

| | | | |
|---|---|---|---|
| 6,484,652 B1* | 11/2002 | Colburn, Jr. | A01B 79/005 111/118 |
| 8,204,689 B2 | 6/2012 | Christy et al. | |
| 8,444,937 B2 | 5/2013 | Tuli et al. | |
| 8,472,023 B2 | 6/2013 | Preiner et al. | |
| 10,345,283 B1* | 7/2019 | Laird | G01N 33/24 |
| 10,564,122 B1* | 2/2020 | Xu | G01N 27/44791 |
| 2003/0009286 A1* | 1/2003 | Shibusawa | A01B 79/005 702/2 |
| 2005/0172733 A1* | 8/2005 | Drummond | A01B 79/005 73/864.41 |
| 2011/0036281 A1* | 2/2011 | Beaujot | A01B 63/16 111/149 |
| 2012/0227992 A1* | 9/2012 | Henry | A01B 63/114 172/4 |
| 2014/0041563 A1* | 2/2014 | Henry | A01B 79/005 111/139 |
| 2015/0289438 A1* | 10/2015 | Sauder | A01B 79/005 701/50 |
| 2016/0037709 A1* | 2/2016 | Sauder | A01C 7/203 700/275 |
| 2017/0049044 A1* | 2/2017 | Stoller | A01C 23/025 |
| 2018/0049361 A1* | 2/2018 | Zemenchik | A01B 63/008 |
| 2018/0160613 A1* | 6/2018 | Kovach | A01B 63/28 |
| 2018/0168094 A1* | 6/2018 | Koch | G01J 5/04 |
| 2019/0075714 A1* | 3/2019 | Koch | G01B 7/26 |

OTHER PUBLICATIONS

"Field-Scale Validation of an Automated Soil Nitrate Extraction and Measurement System", Precision Agriculture, Kevin J. Sibley, et al., Sep. 19, 2008 (7 pages).

"Real-Time Sensing of Soil Nitrate Concentration in the Parts per Million Range While the Soil Is in Motion", Applied Spectroscopy, Jones et al., Sep. 2013 (6 pages).

"Application of FTIR Spectroscopy to Agricultural Soils Analysis", InTech, Linker Raphael, Mar. 1, 2011 (21 pages).

"Simple Determination of Nitrate in Soils by Second-Derivative Spectroscopy", A. Sempere et al., Journal of Soil Science, vol. 44, Issue 4, Jul. 28, 2006 (2 pages).

"Agitated Soil Measurement Method for Integrated On-the-Go Mapping of Soil pH, Potassium and Nitrate Contents", Computers and Electronics in Agriculture 60, Science Direct, B. Sethuramasamyraija et al., Aug. 7, 2007 (14 pages).

"Mid-Infrared Spectroscopic Determination of Soil Nitrate Content", B. R. Jahn et al., Biosystems Engineering, vol. 34, Issue 4, Aug. 2006, (28 pages).

"Nitrate and Organic N Analysis wit Second-Derivative Spectroscopy", William G. Crumpton et al., Limnology and Oceanography, vol. 37, Issue 4, Jun. 1992 (2 pages).

"Review: Infrared Spectroscopy—Enabling an Evidence-Based Diagnostic Surveillance Approach to Agricultural and Environmental Management in Developing Countries", Keith D. Shepherd et al., Journal of Near Infrared Spectroscopy, vol. 15, Issue 1, Feb. 7, 2007 (2 pages).

* cited by examiner

AGRICULTURAL IMPLEMENT AND PROCEDURE FOR ON-THE-GO SOIL NITRATE TESTING

BACKGROUND OF THE INVENTION

1. Field of the Invention

The present invention generally relates to agricultural implements, soil testing and precision farming procedures, and, more particularly, to agricultural implements that can be used for on-the-go, continuous testing of soil nutrients, such as nitrate-N.

2. Description of the Related Art

Precision farming is a term that refers to farming concepts and procedures seeking to apply field inputs in accurate amounts where needed and when needed, without wasteful and potentially harmful over-application. For example, the application of soil nutrients in precision farming involves applying adequate nutrients on a timely basis for plant use, without over applying the nutrients which can lead to unnecessary expense and potential environmental contamination.

Nitrogen in the nitrate form, referred to as nitrate-N, is necessary for good plant growth of many crops, such as corn, but is not stable in the soil profile. Nitrogen based fertilizers and the nitrate-N supplied thereby can leach through the soil rapidly, and are subject to breakdown, transformation, translocation and loss over time as the results of denitrification, nitrification, volatilization, photodegradation and the like. The rates at which such changes occur can vary significantly, depending on, at least in part, the soil types and weather conditions. As a result, available nitrogen in the nitrate form (nitrate-N) is susceptible to significant variations even within relatively small areas of the same growing plot or field, throughout the soil profile vertically, and over relatively short time intervals, and is dependent on other factors, both constant and changing.

It is known that inadequate supply of nitrate-N during early growing stages results in significant risk for potential yield reductions in crops such as corn. Since root penetration is still shallow during early growing stages, the level of nitrate-N concentration in a region near the soil surface is important for this development. As the crop continues to grow and roots penetrate more deeply, the level of nitrate-N concentration at greater depths becomes more useful and important.

In response to the competing factors mentioned above and other factors, farmers often compensate prophylactically by over-applying nitrogen fertilizers early in the crop growing cycle, including during the Fall before Spring planting, in an effort to ensure that sufficient nitrate-N is available when needed by the crop. Subsequent applications by side dressing with nitrogen fertilizers during the crop growing cycle may supply needed nitrate-N in some areas of a field, but also may add to unnecessary over-application in other areas of the same field. Scouting techniques to improve pre-season and in-season nitrogen fertilization strategies and methodologies are still evolving. Both under application and over application conditions can exist within relatively small areas when a constant rate of fertilizer is applied over the areas, and both can result in suboptimal crop yields. It has been estimated that only about 40-60% of the nitrogen fertilizer applied in corn fields is actually used by the corn crops grown. Even with recent improved genetics and stay-green qualities of non-legume crops, which extend the ear-field period in corn, the utilization rate has improved only minimally. The excess nitrogen that is applied but not used by the growing crops is not only a wasted expense but also a potential source for surface and groundwater contamination.

Testing for nitrate-N concentration in soils has been inconvenient and expensive. The procedure traditionally involves measuring soil nitrate-N concentration after obtaining discrete soil samples and transferring the samples to a laboratory for testing. Since nitrate-N concentration can vary significantly even over a short time interval depending on other conditions, such as actually experienced weather conditions and even man-influenced conditions such as irrigation, crop rotations and subsequent fertilizer or manure application; and, since different soil types respond differently to these differing conditions, obtaining sufficient soil samples for laboratory testing to generate an accurate soil map of existing nitrate-N concentrations has been expensive and somewhat impractical. The time delay alone resulting from laboratory testing diminishes the accuracy of the information for precision farming techniques, since the actual then-existing nitrate-N concentrations may differ significantly from the samples taken in the same location. Further, since the soil types and field conditions can vary significantly even in small areas, an accurate nitrate-N map requires a large amount of discrete soil samples for testing. Remote sensing techniques are still evolving, but do not always detect nitrogen deficiency in crops until it is too late and a potential yield reduction has occurred.

More recently, on-the-go nitrate-N sensors have been proposed for use on tillage shanks pulled through the soil for continuous, in situ soil nitrate-N testing. The sensors of one proposed use are configured for transient infrared reflectance spectroscopy (TIRS). The sensors target a specific energy or light frequency at the soil through a small diamond or sapphire lens embedded into or incorporated with the tillage shank. Combining the on-the-go sensor with existing field mapping technology can generate a nitrate-N map used by a variable applicator for simultaneous or subsequent application of nitrogen-based fertilizers in more precisely controlled amounts to meet specific crop requirements on a timely basis, while recognizing existing field conditions.

Many agricultural implements carry shanks for soil bed preparation. Fertilizer applicators can carry shallow-penetrating shanks to prepare the soil to receive solid, liquid, and/or gaseous fertilizer. Sub-soilers can carry shanks which extend into the soil more deeply, to break up a compaction layer, which is also referred to as a hardpan, to promote improved root penetration by the crops. It is known to control and vary the penetration depths of soil preparation shanks in some agricultural implements.

What is needed in the art is a reliable and convenient way for a user to determine soil nitrate-N level, as distinguished from total nitrogen level from various nitrogen forms throughout the soil depth profile that is relevant to the crop being grown or to be grown.

SUMMARY OF THE INVENTION

The agricultural implement and procedure for on-the-go soil nitrate-N testing disclosed herein deploys a nitrate-N sensor or sensors at different soil penetration depths in one or several passes to obtain accurate nitrate-N level information throughout the root zone of a crop growing or to be grown in the tested area. This may occur at any time of the year suitable to the conditions present.

The agricultural implement and procedure for on-the-go soil testing disclosed herein, in one form, is directed to an agricultural implement having a chassis, at least one shank carried by the chassis, the shank including a shank body configured to penetrate a soil surface. At least one on-the-go sensor is operatively deployed on the shank body. A depth control mechanism is configured for deploying the at least one sensor at different selected operating depths including at least at a first depth within a first zone and at a second depth within a second zone. This implement can be configured to include a single sensor deployed at the first depth while being moved through the first zone and thereafter at the second depth while being moved through the second zone, a single sensor moved between the first and second depths while traveling along a path between the first and second zones, or first and second complementary sensors deployed at the first and second depths in the first and second zones simultaneously.

The agricultural implement and procedure for on-the-go soil nitrate-N testing disclosed herein, in another form thereof, is directed to a soil testing procedure for field testing nitrate-N in a soil. The procedure includes providing an agricultural implement with a chassis, at least one shank carried by the chassis and configured to penetrate a surface of the soil, and at least one on-the-go nitrate-N sensor operatively deployed on the shank; deploying and operating the at least one nitrate-N sensor at a first depth and determining a nitrate-N condition in a first depth zone of the soil; and deploying and operating the at least one nitrate-N sensor at a second depth and determining a nitrate-N condition in a second depth zone of the soil.

An advantage of the agricultural implement and procedure for on-the-go soil nitrate-N testing as disclosed herein is that the levels of nitrate-N in the soil can be determined at different soil depths relevant to the root zone of a crop growing or to be grown in the tested area. This allows the nitrate-N supply and any downward potential nitrate movement (i.e. leaching) within the root zone to be characterized and predicted to depth, to develop optimized placement and application rate strategies.

Another advantage of the agricultural implement and procedure for on-the-go soil nitrate-N testing disclosed herein is the promotion of precision farming by facilitating more accurate and timely fertilizer application from more accurate nitrate-N concentration level information. This information may be used to construct field nitrate-N prescriptions, and subsequent as-applied maps.

Still another advantage of the agricultural implement and procedure for on-the-go soil testing disclosed herein is that the testing procedure can be incorporated with existing soil preparation technology involving a range of nitrate-N application tools and mapping.

BRIEF DESCRIPTION OF THE DRAWINGS

The above-mentioned and other features and advantages of this invention, and the manner of attaining them, will become more apparent and the invention will be better understood by reference to the following description of several embodiments of the invention taken in conjunction with the accompanying drawings, wherein.

Corresponding reference characters indicate corresponding parts throughout the several views. The exemplification set out herein illustrates one embodiment of the invention and such exemplification is not to be construed as limiting the scope of the invention in any manner.

DETAILED DESCRIPTION OF THE INVENTION

Figure 1:
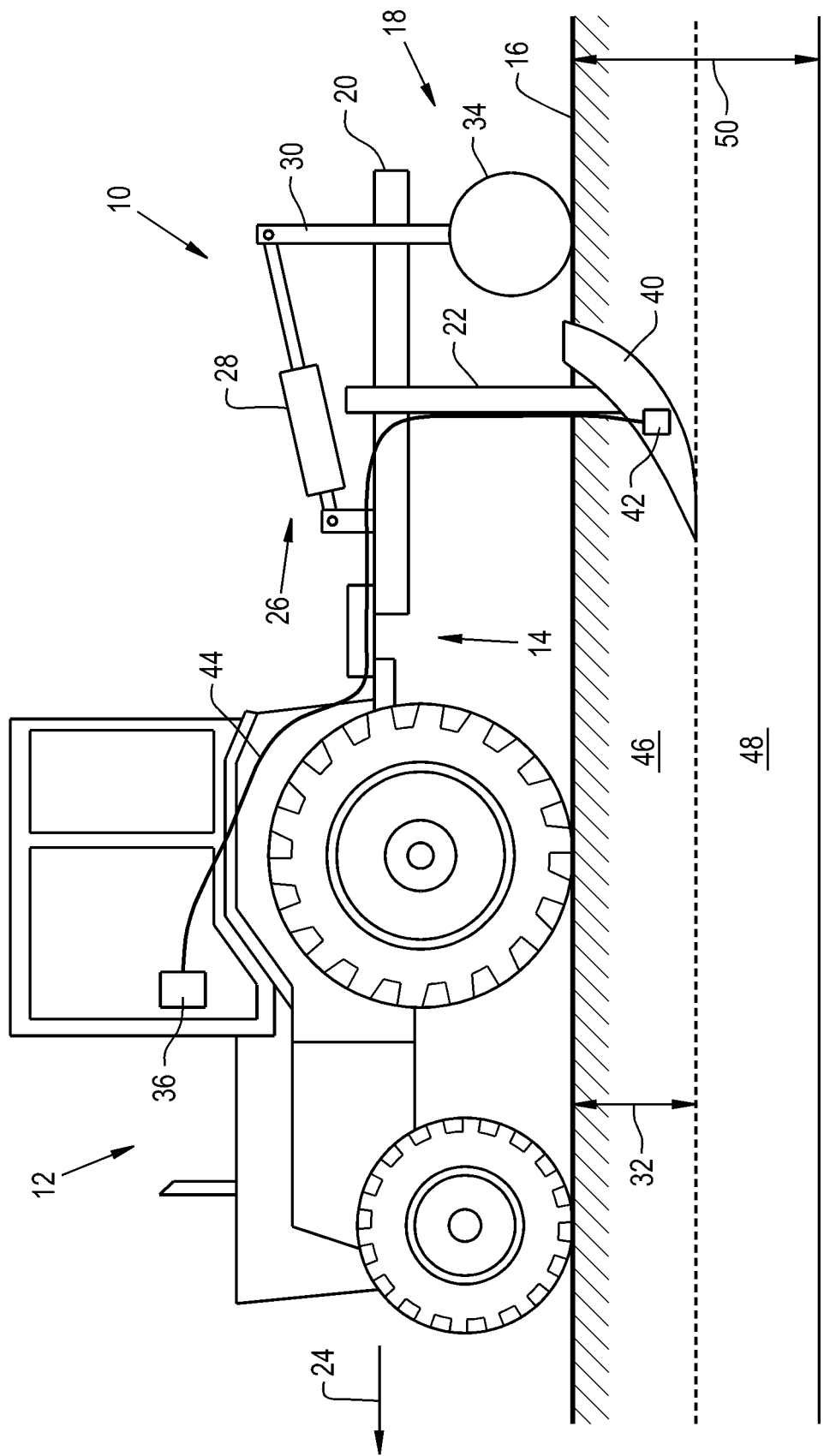
FIG. 1 is a side view of an embodiment of an agricultural implement embodying the present invention, depicting a first adjusted operating position for the implement.

Referring now to the drawings and in particular to FIG. 1 of the drawings, an embodiment of an agricultural implement 10 is shown. Implement 10 is configured for conducting an on-the-go nitrate-N testing procedure when implement 10 is towed behind a work vehicle, such as an agricultural tractor 12. In the illustrated embodiment, implement 10 is coupled to tractor 12 by a suitable hitch mechanism 14, including hitch structures of both implement 10 and tractor 12, for connecting implement 10 and tractor 12 mechanically for towing and electrically and/or hydraulically for adjusting and operating implement 10 from tractor 12, including adjusting and controlling an operating position of implement 10 relative to a soil surface 16 upon which it is operated. The manner by which implement 10 is coupled to tractor 12 for towing and control during operation is well known by those skilled in the art. It should be understood that implement 10 also can be towed behind other types of work vehicles. Still further, it should be understood that implement 10 also can be self-powered by an internal combustion engine or other power source, if desired.

Implement 10 includes a chassis 18 that carries an implement frame 20 configured to support at least one and commonly multiple tools, such as a shank 22. In this configuration, the shank 22 faces oncoming soil as implement 10 is towed in a direction of travel indicated by arrow 24. Shank 22 is supported by a depth control mechanism 26, which can include an actuator 28 and a suitable linkage mechanism 30 whereby adjustment of actuator 28 increases or decreases a penetration depth 32 of shank 22 beneath soil surface 16. Actuator 28 can be a linear actuator, such as a hydraulic or pneumatic cylinder, an electromechanical actuator, a rotary actuator such as a hydraulic or electric servo, or an actuator of other types. Suitable structures and arrangements for depth control mechanism 26 are well-known to those skilled in the art and will not be described in further detail herein. Alternatively, the penetration depth of the shank 22 may be adjusted in other ways, including other types of connecting arrangements between implement 10 and tractor 12 whereby a vertical position of the implement frame 20 relative to the tractor 12 can be varied to adjust the penetration depth 32 of the shank 22. In addition, as the height of the frame 20 above the soil surface 16 changes, a wheel assembly 34 may adjust a vertical position of a gauge wheel (not shown) relative to the frame 20, thereby enabling the wheel assembly 34 to support the frame 20 throughout the range of vertical frame movement.

It should be appreciated that a separate actuator 28 also can be connected directly to the shank 22 to selectively adjust the penetration depth 32 of the shank 22 while another actuator or other actuators (not shown) are connected to other shanks (not shown) for controlling the penetration depths thereof. The actuator or actuators 28 can be coupled to a controller 36 configured to control the actuator 28. The controller 36 also can be coupled to other components of the implement 10 to control operation of various aspects of the implement 10.

Shank 22 includes a shank body 40 which is configured to partially or completely penetrate the soil surface 16, and an on-the-go sensor 42 attached to or carried by shank body 40. On-the-go sensor 42 has a data transmission connection 44 to controller 36 whereby data gathered by sensor 42 is transmitted to controller 36 for further processing, such as to generate a field map of existing nitrate-N conditions, for calculating and/or mapping application rates for nitrogen to be applied based on the existing nitrate-N conditions, and/or for controlling the operation of implement 10 and/or another implement (not shown) such as a variable fertilizer applicator. Including calculating a rate for the application of nitrogen based on the determined nitrate-N conditions in the first and second depth zones 46, 48.

The shank body 40 can be of known construction, having a generally curved structure descending down toward the soil surface 16 during operation, as shown, or having any other suitable construction that allows the shank body 40 to penetrate the soil surface 16 during operation of the implement 10. The shank body 40 can also have a generally rectangular cross-section. It should be appreciated that the shape and size of the shank body 40 can be adjusted as desired in order to better carry out the functionality of the agricultural implement 10, whether the agricultural implement 10 is a field cultivator, a fertilizer applicator, a subsoiler, a specialized soil testing implement, etc.

The on-the-go sensor 42 is attached to shank body 40 to accumulate data relative to nitrate-N concentration in a first depth zone 46 when shank 22 is operated at first penetration depth 32. Generally, the position of on-the-go sensor 42 within the first zone 46 is at the midpoint of the first zone 46. For example, if the first zone 46 is defined as being the first 12 inches of soil below soil surface 16, on-the-go sensor 42 is pulled through the soil at a depth of about 6 inches. On-the-go sensor 42 can effectively sense one or more desired parameters. For example, the on-the-go sensor 42 can be configured as an optical sensor configured and operating to use transient infrared reflectance spectroscopy (TIRS) of the type described previously herein, which allows emitted light from the sensor to contact soil adjacent to a window to determine a concentration of nitrate-N in the soil within first zone 46. It should be appreciated that various sensors can define differing probing areas, depending upon the configuration of the sensor, which can be adjusted as desired to sense different parameters of soil adjacent to the sensor as the sensor is carried by the shank body 40.

Figure 2:
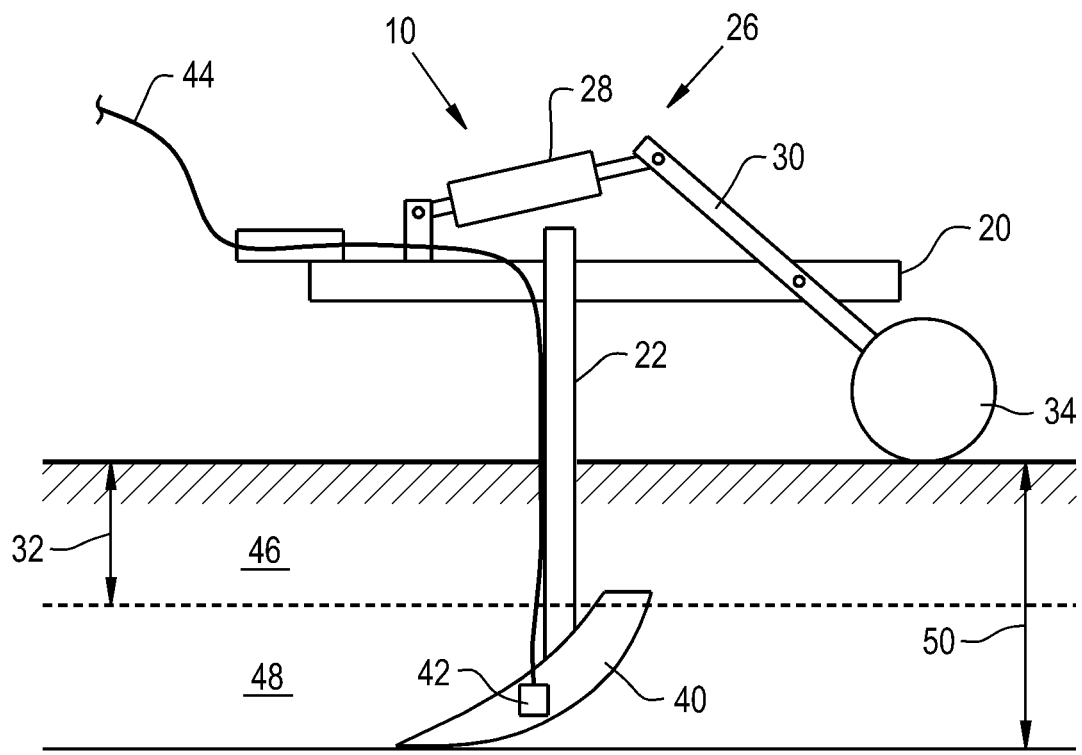
FIG. 2 is a fragmentary side view of the agricultural implement of FIG. 1, depicting a second adjusted operating position for the implement.

Desirably, implement 10 also ascertains data sufficient to determine the desired parameter in a second depth zone 48 immediately below first zone 46. This can be accomplished in several ways using one or several shank bodies and one or several on-the-go sensors. FIG. 2 depicts the aforedescribed shank body 40 and on-the-go sensor 42 operated at a second penetration depth 50 below soil surface 16. For example, second zone 48 can be a next layer of soil beneath first zone 46, that is, a layer that is generally from about 12 inches to about 24 inches below soil surface 16. Desirably, on-the-go sensor 42 is operated at about the midpoint of second zone 48, or, in the example stated at about 18 inches below soil surface 16 when second zone 48 extends from 12 to about 24 inches below soil surface 16. In the embodiment illustrated in FIGS. 1 & 2, implement 10 can be towed by a tractor 12 over a field in two passes. During a first pass on-the-go sensor 42 is carried in first zone 46 as described, and during a second pass, on-the-go sensor 42 is carried in second zone 48 as described.

Figure 3:
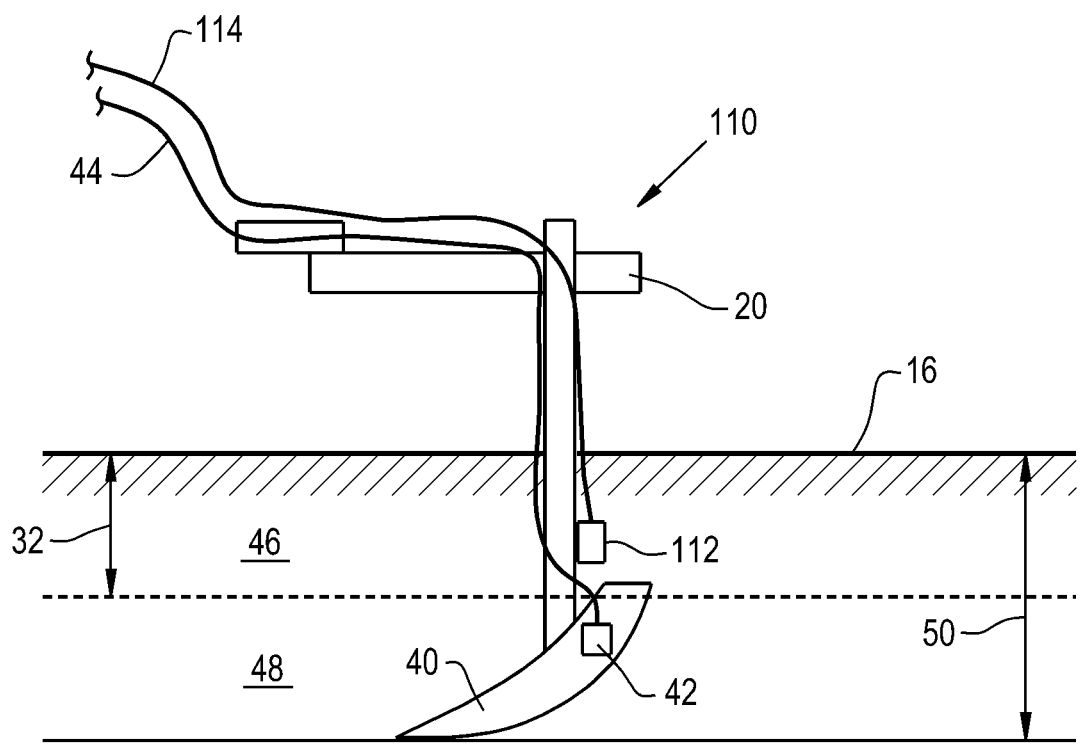
FIG. 3 is a fragmentary side view of another embodiment of an agricultural implement embodying the present invention.

Nitrate-N concentration of first zone 46 and a second zone 48 can be ascertained also by the use of multiple on-the-go sensors carried at different positions on a single shank body. FIG. 3 shows an implement 110 similar to implement 10, having a shank body 40 and an on-the-go sensor 42 as described previously. Implement 110 differs from implement 10 in that shank body 40 also carries a second on-the-go sensor 112 also coupled to controller 36 by a data transmission connection 114. One on-the-go sensor is pulled through the ground within first zone 46 and the second on-the-go sensor is pulled through the ground within second zone 48. The use of implement 110 differs from the use of implement 10 in that multiple passes of implement 110 over a field are not required to determine nitrate-N concentration within first and second zones 46, 48. Testing is done in both first zone 46 and second zone 48 during one pass of implement 110 over a field.

Figure 4:
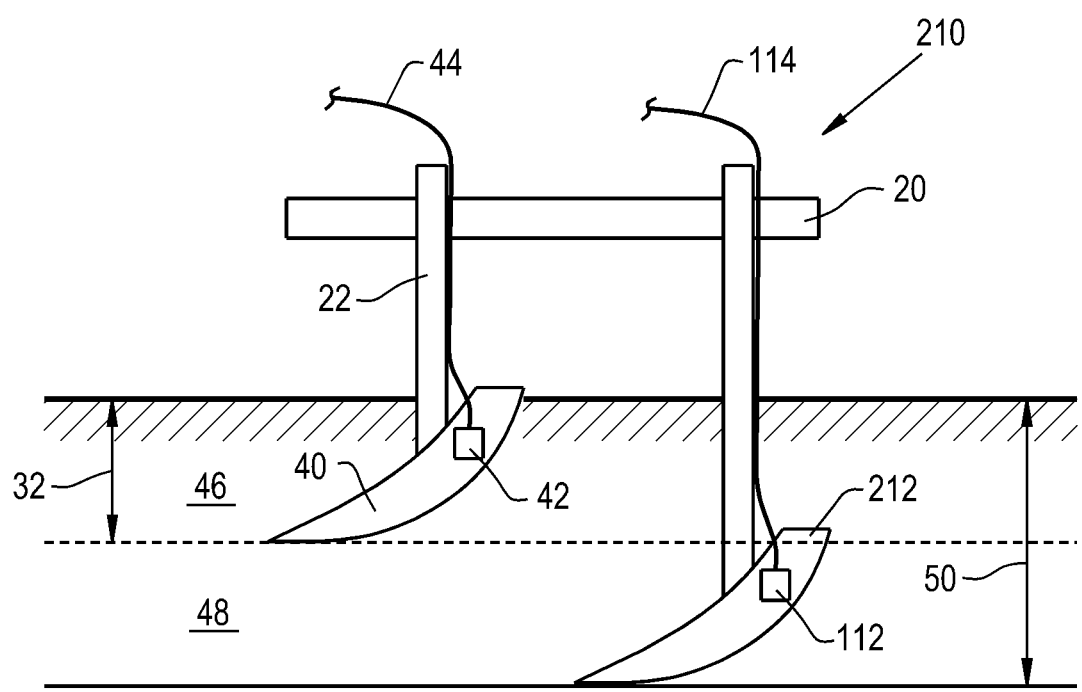
FIG. 4 is a fragmentary side view of yet another embodiment of an agricultural implement embodying the present invention.

Nitrate-N concentration of first zone 46 and second zone 48 can be ascertained in yet other ways. FIG. 4 illustrates yet another embodiment of an agricultural implement 210 that is similar to implement 10, having a shank body 40 and an on-the-go sensor 42 as described previously. Implement 210 differs from implement 10 in that a second shank body 212 carries the second on-the-go sensor 112. Again, one on-the-go sensor is pulled through the ground within the first zone 46, with shank body 40 generally at first penetration depth 32, and the second on-the-go sensor 112 is pulled through the ground within second zone 48, with second shank body 212 generally at second penetration depth 50. As with implement 110, testing is done in both first and second zones 46, 48 simultaneously, during one pass of implement 210 over a field.

While the various embodiments have been described such that second zone 48 is tested in one way or another by pulling either first on-the-go sensor 42 or second on-the-go sensor 112 at about the midpoint of second zone 48, it should be understood that with some implements and under some conditions either shank body 40 or shank body 112 may not be capable of reaching a sufficient depth to place the first or second on-the-go sensors at the midpoint of the second zone 48. In such situations, data accumulated at the maximum penetration depth can be used to calculate the concentration within the second zone 48. It should be understood still further, that from the data acquired relative to first zone 46 and a second zone 48 the concentration in yet a deeper zone beneath second zone 48 can be calculated. The defined zones can correspond to recognized nutrient stratification phenomenon, to facilitate prediction of nutrient depletion and fertilization requirements. While such stratification depends on soil types and other conditions, a baseline nitrogen-N can be ascertained and applied in the prediction models by using the aforedescribed implements and procedures. Subsequent verification of the models can be obtained while applying subsequent applications of fertilizer.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A soil testing procedure for field testing nitrate-N in soil, comprising the steps of:
   providing an agricultural implement with a chassis, a first shank and a second shank carried by the chassis and each shank configured to penetrate a surface of the soil, and at least one on-the-go nitrate-N sensor operatively deployed each first shank and second shank;
   deploying and operating the first shank and the at least one on-the-go nitrate-N sensor thereon at a first depth in a first depth zone in the soil and simultaneously deploying and operating the second shank and the at least one on the go nitrate-N sensor thereon at a second depth in a second depth zone in the soil, wherein the second depth zone is deeper than the first depth zone;
   determining a nitrate-N condition in the first depth zone of the soil, determining a nitrate-N condition in the second depth zone of the soil; and
   calculating a rate for an application of nitrogen based on the determined nitrate-N conditions in the first and second depth zones;
   mapping an area to display existing nitrate-N conditions; and
   mapping an area to display rates of nitrogen to be applied based on the nitrate-N conditions determined in the determining steps;
   wherein the first shank and the at least one on-the-go nitrate-N sensor thereon is deployed in the first depth zone and operated in a travel direction in front of and above the second shank, and the second shank and the at least one on-the-go nitrate-N sensor thereon is deployed in the second depth zone and operated in the travel direction below and behind the first shank.

2. The soil testing procedure of claim 1, wherein the at least one on-the-go nitrate-N sensor includes a sensor configured for transient infrared reflectance spectroscopy.

3. The implement according to claim 1, wherein the at least one on-the-go sensor positioned on the first shank include two on-the-go nitrate-N sensors, and wherein the at least one on-the-go sensor positioned on the second shank include two on-the-go nitrate-N sensors.

* * * * *